United States Patent [19]
Lindström et al.

[11] Patent Number: 5,879,325
[45] Date of Patent: Mar. 9, 1999

[54] METHOD AND DEVICE FOR ADMINISTERING OR ASPIRATING SUBSTANCES ALONG THE WHOLE GASTROINTESTINAL TRACT

[75] Inventors: Kjell Olof Torgny Lindström, SE-23636 Hölluiken; Karl Gunnar Wiking Mánsson, S-23731 Bjärred; Lars Olof Emil Nyberg, SE-22652 Lund, all of Sweden

[73] Assignees: Kjell Olof Torgny Lindstrom, Hollviken; Karl Gunnar Wiking Mansson, Bjarred; Lars Olof Emil Nyberg; Olof Borga, both of Lund, all of Sweden

[21] Appl. No.: 875,135

[22] PCT Filed: Feb. 9, 1996

[86] PCT No.: PCT/SE96/00167

§ 371 Date: Jul. 17, 1997

§ 102(e) Date: Jul. 17, 1997

[87] PCT Pub. No.: WO96/25085

PCT Pub. Date: Aug. 22, 1996

[30] Foreign Application Priority Data

Feb. 13, 1995 [SE] Sweden ................... 9500498

[51] Int. Cl.⁶ .............................. A61M 31/00
[52] U.S. Cl. ................... 604/49; 604/264; 604/270
[58] Field of Search .................. 604/93, 49, 53, 604/54, 27, 35, 36, 38, 48, 264, 280, 270

[56] References Cited

U.S. PATENT DOCUMENTS

| | | | |
|---|---|---|---|
| 2,464,933 | 3/1949 | Kaslow | 604/270 |
| 2,773,502 | 12/1956 | Kaslow et al. | 604/93 |
| 4,613,323 | 9/1986 | Norton et al. | 604/43 |
| 4,631,054 | 12/1986 | Kim | 604/54 |
| 5,391,158 | 2/1995 | Peters | 604/265 |

FOREIGN PATENT DOCUMENTS

| | | | |
|---|---|---|---|
| 2046595 | 4/1980 | United Kingdom . | |
| 2046595 | 11/1980 | United Kingdom | A61M 25/00 |
| 9205759 | 4/1992 | WIPO | A61J 3/07 |
| WO92/05759 | 4/1992 | WIPO . | |

*Primary Examiner*—Wynn Wood Coggins
*Assistant Examiner*—Deborah Blyveis
*Attorney, Agent, or Firm*—Ladas & Parry

[57] ABSTRACT

The invention relates to a method for introducing a tube (3) in order to deliver or remove substance(s) at positions in the gastrointestinal tract by letting a human subject or an animal swallow a firm body (1), the "bead part", to which said tube is fastened and letting the head part (1) be moved by peristalsis to desired positions. According to the invention, said head part (1), which is provided with a bore (2) or cavity running through it and being in fluid connection with said tube (3), is halted at a selected position in any part of the gastrointestinal tract by fixing the tube at the entrance into the body or outside the body. Said tube (3) is marked to indicate length of the swallowed part of the tube in order to guide the finding of said selected position. Liquid or gas is delivered or aspirated through said tube (3) and said bore (2) or cavity running through the head part (1).

27 Claims, 7 Drawing Sheets

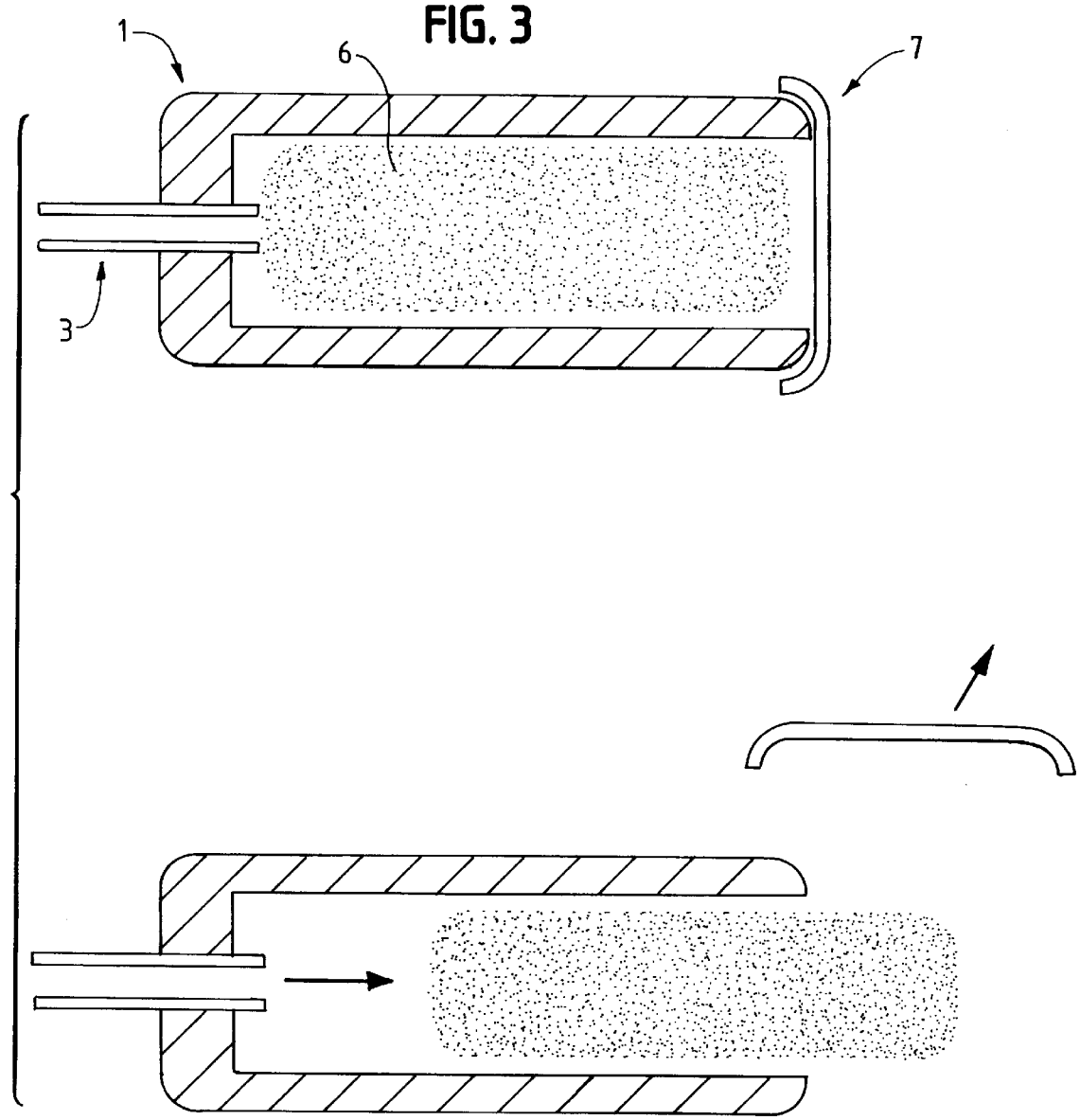

METHOD AND DEVICE FOR ADMINISTERING OR ASPIRATING SUBSTANCES ALONG THE WHOLE GASTROINTESTINAL TRACT

TECHNICAL FIELD OF THE INVENTION

This invention relates to a method for introducing a tube in order to deliver or remove substance(s) at positions in the gastrointestinal tract by letting a human subject or an animal swallow a firm body, hereafter called "head part", to which said tube is fastened and letting the head part be moved by peristalsis to desired positions.

BACKGROUND TO THE INVENTION

It is often of considerable interest and value to be able to administer substances at predetermined locations all along the gastrointestinal (GI-)tract. The same applies to the possibility of aspirating samples or collect measurement signals from different sensors. It is also of interest to test the local permeability all along the GI-tract to investigate new possibilities to develop pharmaceutical preparations or to obtain a better understanding about the kinetics of a certain drug. It is also possible to sample through the tube for analysis of possible deviations in the composition of the gastric or intestinal juice. It can further be of interest to measure some parameter, e.g. pH, pressure, electrolytes, a chemical compound or enzyme at a specified location along the GI-tract.

Today, a number of capsules are described or are available, which can be swallowed freely (without wire or tube) and which can be tracked telemetrically or by X-ray, isotopes or ultrasound during their ride along the GI-tract. Using this kind of capsules it is possible to deliver an isolated dose of some drug (Hugemann, DE 29 28 477 B2; U.S. Pat. Off.: Casper et al., U.S. Pat. No. 5,170,801 and Kambara et al., U.S. Pat. No. 4,507,115; Hemmati 1969; N.Y. State University 1992) and record and transmit signals for measurement of pH (Wolff and Russ 1960) or pressure (Connell and Rowlands 1960; Bárány and Jacobsson 1964; Farrar and Bernstein 1968). It is also possible to aspirate a small volume of liquid (Uchiyama et al. 1980). A special form of telemetric capsule can by choice of suitable module, designed to be installed onto a basic capsule, deliver a single dose of selected drug, aspirate a small volume, or sample a small biopsy from the intestinal mucosa (Lambert et al. 1991). However, all of these capsules suffers from the limitation that they are mobile along the GI-tract and that they cannot deliver dose or aspirate repeatedly or continuously. The subject who has swallowed the capsule will also experience a limited mobility due to the need for telemetric recording.

Solid bodies fitted with a wire for "mooring" in a fixed position have been described for delivery of a drug from one or multiple pills mounted (a) at the end of the wire or along the wire in the GI-tract (U.S. Pat. Off: Millard, U.S. Pat. No. 2,483,098 and Kaslow and Saputo U.S. Pat. No. 2,773,502) or in the form of a capsule for pressure recording (Browning et al. 1981) or a capsule for delivery of physiologically active or diagnostic substances to the gastrointestinal tract (Lindström et al. Patent application WO 92/05759 A1). These devices can be locked in a fixed position but cannot deliver a solution, time-control dose delivery/aspiration nor execute these operations repeatedly or continuously during a certain time period or at different positions.

A principle for perfusion of the upper part of the small intestine (Lennernäs et al. 1992) is applied using a rather thick tube (diameter 5.3 mm) which is introduced into the intestine under X-ray guidance. The tube contains channels which on one hand allow for inflation of two balloons which lock up one segment of the intestine, on the other hand allow for perfusion of the trapped part of the intestine. In this way is it possible to convey substances in solution and also take back remaining, not absorbed substance or endogenous compounds. The method calls for local anesthesia of the pharynx region and will strongly interfere with the peristalsis and physiology in the GI-tract. Furthermore, the experiments cannot be going on for more than a few hours and only the upper part of the small intestine is accessible (risk for ileus if the thick tube is transported further down into the intestine).

Methods using some form of capsule applied to a tube are described. The so called Watson-capsule (Ferraris Medical Ltd, London, UK), is a solid capsule which is pulled down in the upper small intestine dragging an air-filled tube. It has a very limited application (biopsies in the upper small intestine). Another application is a tube applied with loops in the top which will allow the intestine to get a good grip to pull down the tube. In that way one will obtain a route for application of nutrients into the upper part av the small intestine postoperatively (Bengmark et al. 1989). A similar use has an equipment consisting of a tube with a stabilizing inner thread surrounded by an inflatable balloon (Lauterjung. Patent specification SE 448 671 B). It is introduced in a deflated shape, then filled with liquid to allow transport to the upper small intestine. By increasing the pressure of the liquid the balloon opens and the tube can be used for nutrition. These equipments are not useful for deeper positions. A further application is so called enteroscopy, where a mercury- or air-filled balloon is used to pull down a tube (Deyhle et al. 1972) or a flexible enteroscope (Seensalu 1993). In the first case the tube is utilized for guiding a fiberscope down into the lower part of the small intestine, in the latter the enteroscope is directly used to reach the lower small intestine. These methods are not constructed for administration/aspiration or entrance into the colon and would be very inconvenient for ambulant patients or subjects in normal activity or for administration controlled by the subject itself.

BRIEF DESCRIPTION OF THE INVENTIVE CONCEPT

The present invention aims at creating a method for delivering or removal of substances at selected levels along the whole GI-tract as described in the introductory clause of the attached main claim and necessary equipment to achieve this purpose. A great advantage of the invention is that it enables a repeated or continuous procedure which can be performed on different levels of the gut.

This is obtained by swallowing a firm body (the "head part") which is provided with a bore or cavity running through it and being in fluid connection with a flexible tube. The head part is halted at a selected position in any part of the gastrointestinal tract by fixing the tube at the entrance into the body or outside the body. The tube is marked to indicate length of the swallowed part of the tube in order to guide the finding of said selected position. Liquid or gas is delivered or aspirated through said tube and said bore or cavity. If necessary, the tube and the surrounding gut are made visible by X-ray or other radiation by injecting a (contrast) medium through the tube and the head part. If desired, the head part is allowed to move on to new selected positions and the described events are repeated. The head part and the tube are allowed to leave the gut via the anus.

In a preferred embodiment the head part is opaque to X-ray and the tube is made by polyethene. The outer surface of the tube can have scale marks to indicate the distance from the lips or nostrils down to the position of the head part. The tube outside the body is kept in a small reel placed, for instance, in a breast pocket of the subject. The external part of the tube has an interface for connection to, e.g. an injection syringe used for delivering solution to the gut or aspirating liquid from it.

Even if parts of our invention can be found in some earlier methods, none has the simplicity and ease that our invention has, regarding the combination of facile introduction of the head part and tube into the GI-tract, of anchoring the head part or allowing the subject to move freely. The method to deliver or aspirate repeatedly or continuously and at repeated locations is without counterpart. Using a tube with a scale enables a high degree of accuracy in positioning along the GI-tract without use of any medical imaging modality once the "geography" of a subject's gut is known. No hitherto described method or equipment allows delivery of solid substance, which is a very important aspect, for instance when the substance has a low solubility.

BRIEF DESCRIPTION OF APPENDED DRAWINGS

Seven Figures are accompanying the application.

FIG. 3 shows a longitudinal section of a head part used for administration of substance powder.

DETAILED DESCRIPTION OF A PREFERRED EMBODIMENT

Figure 1:
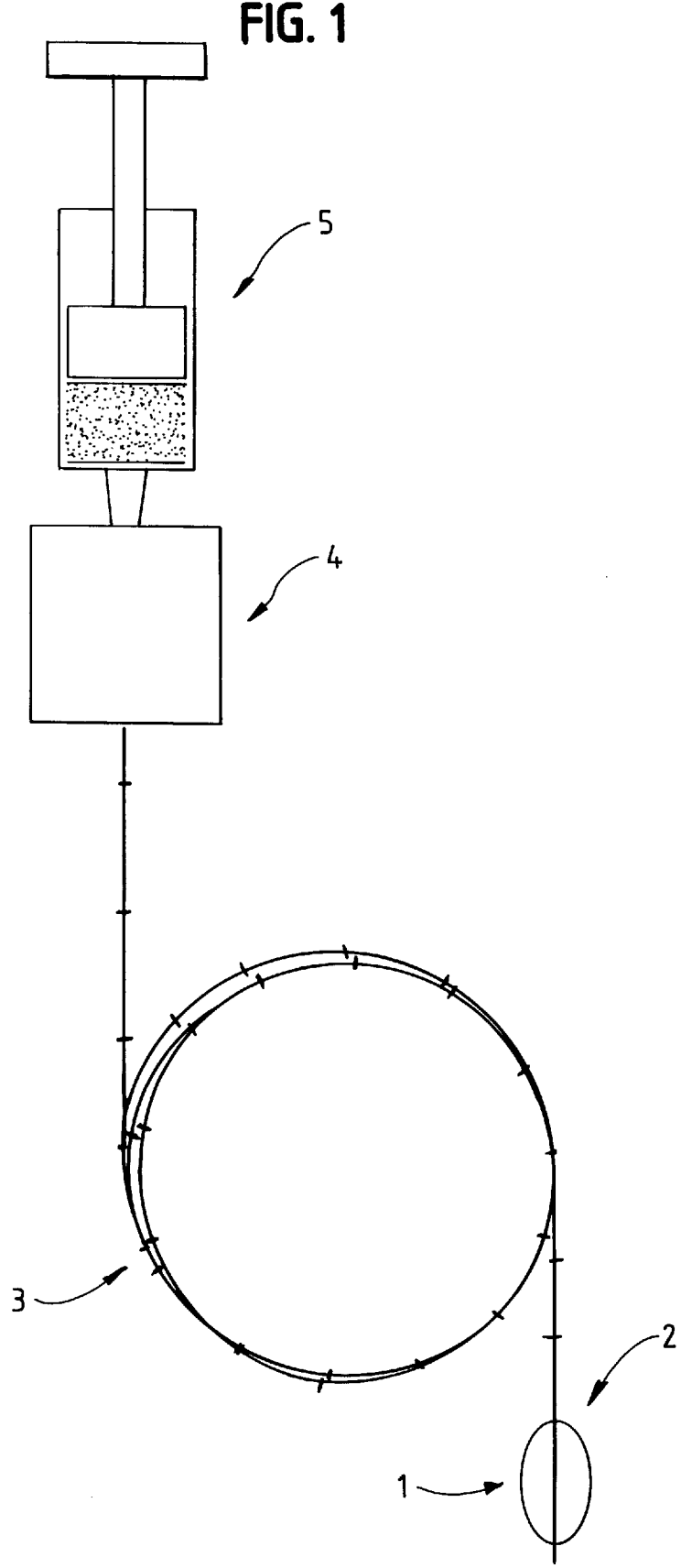
FIG. 1 shows a preferred embodiment.
Figure 2A:
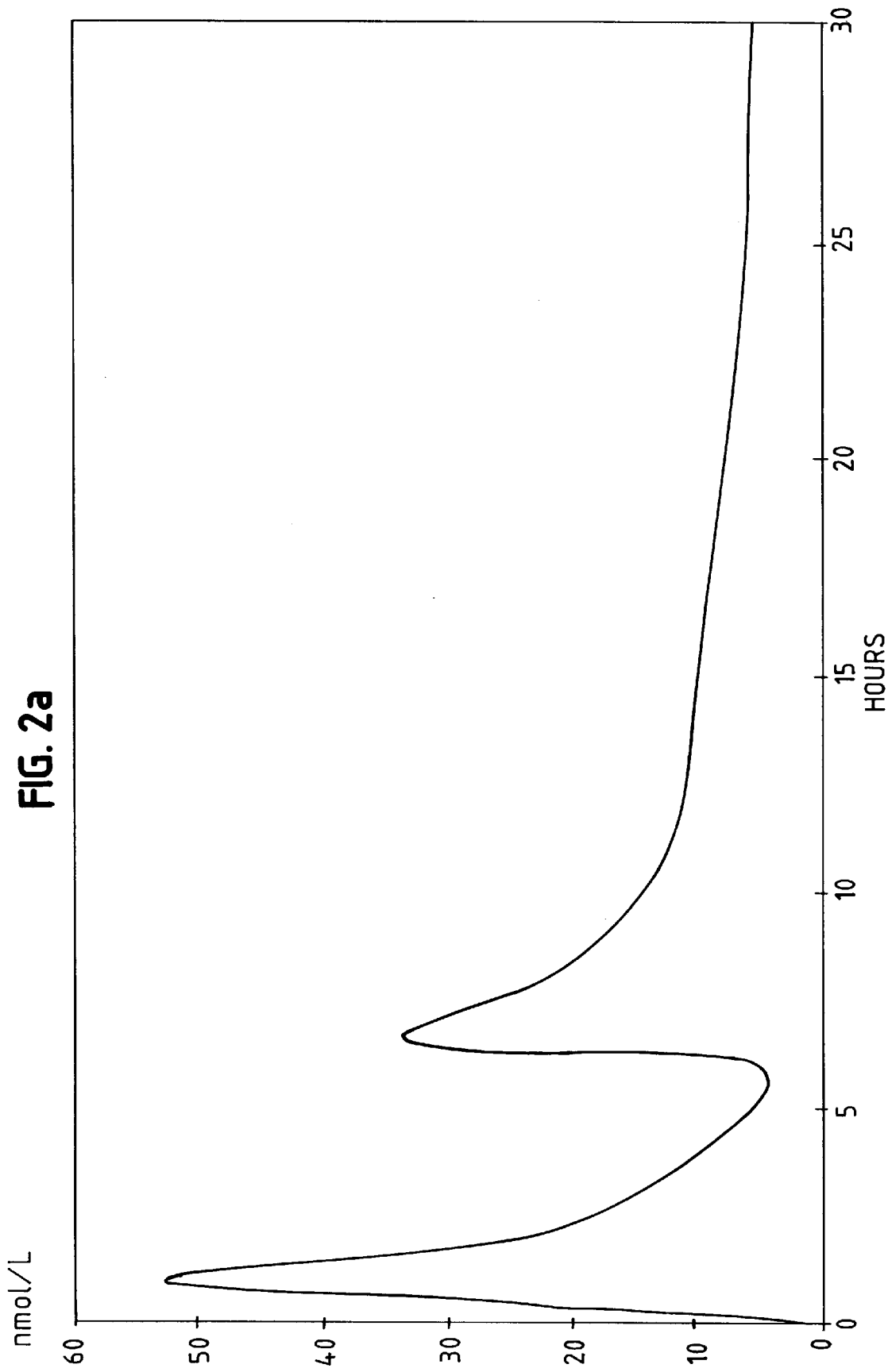
FIGS. 2a–2d illustrate plasma concentrations in 4 subjects after administration of a dissolved drug substance using the preferred embodiment at different levels of the GI-tract.
Figure 2B:
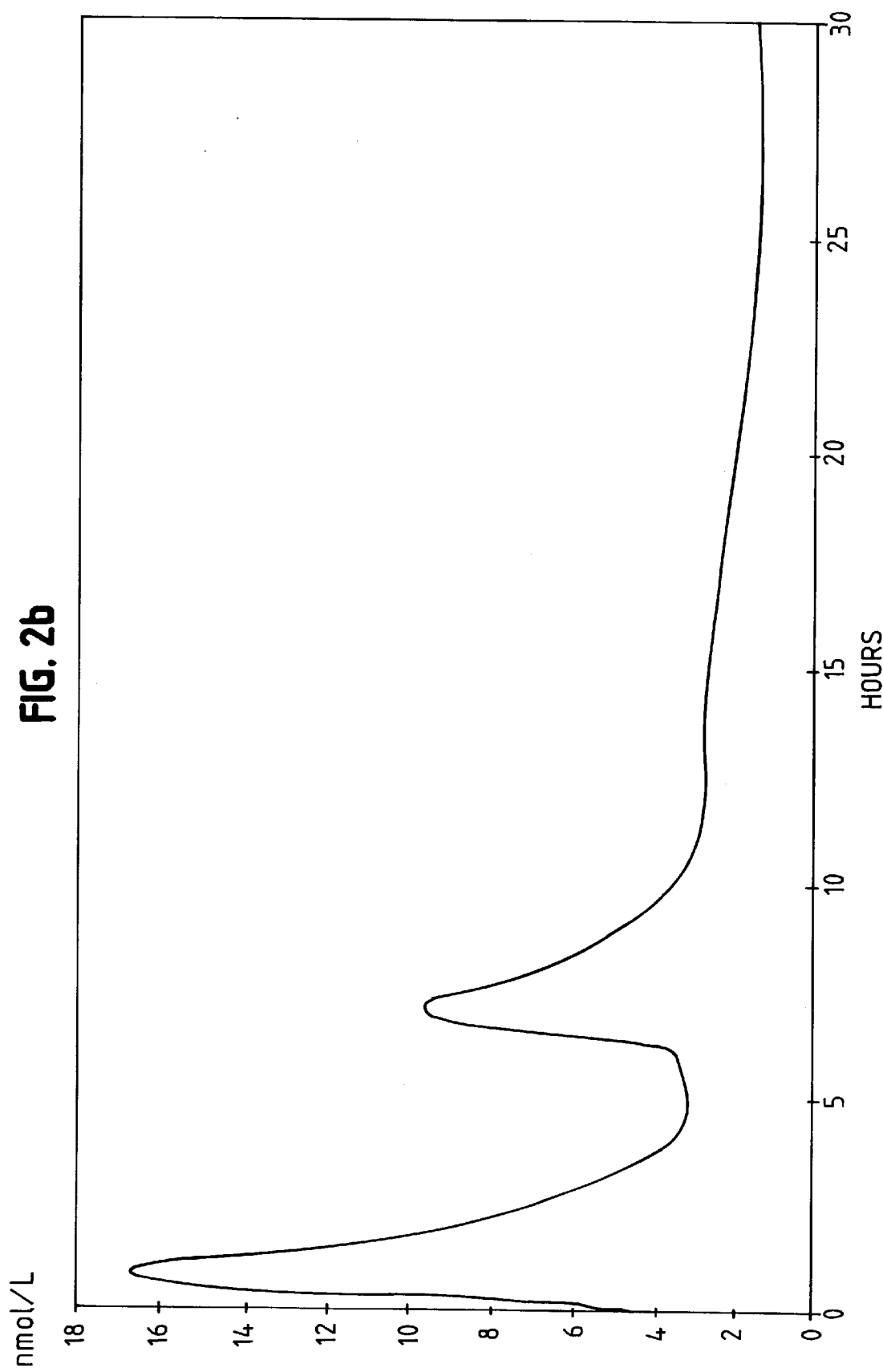
Figure 2C:
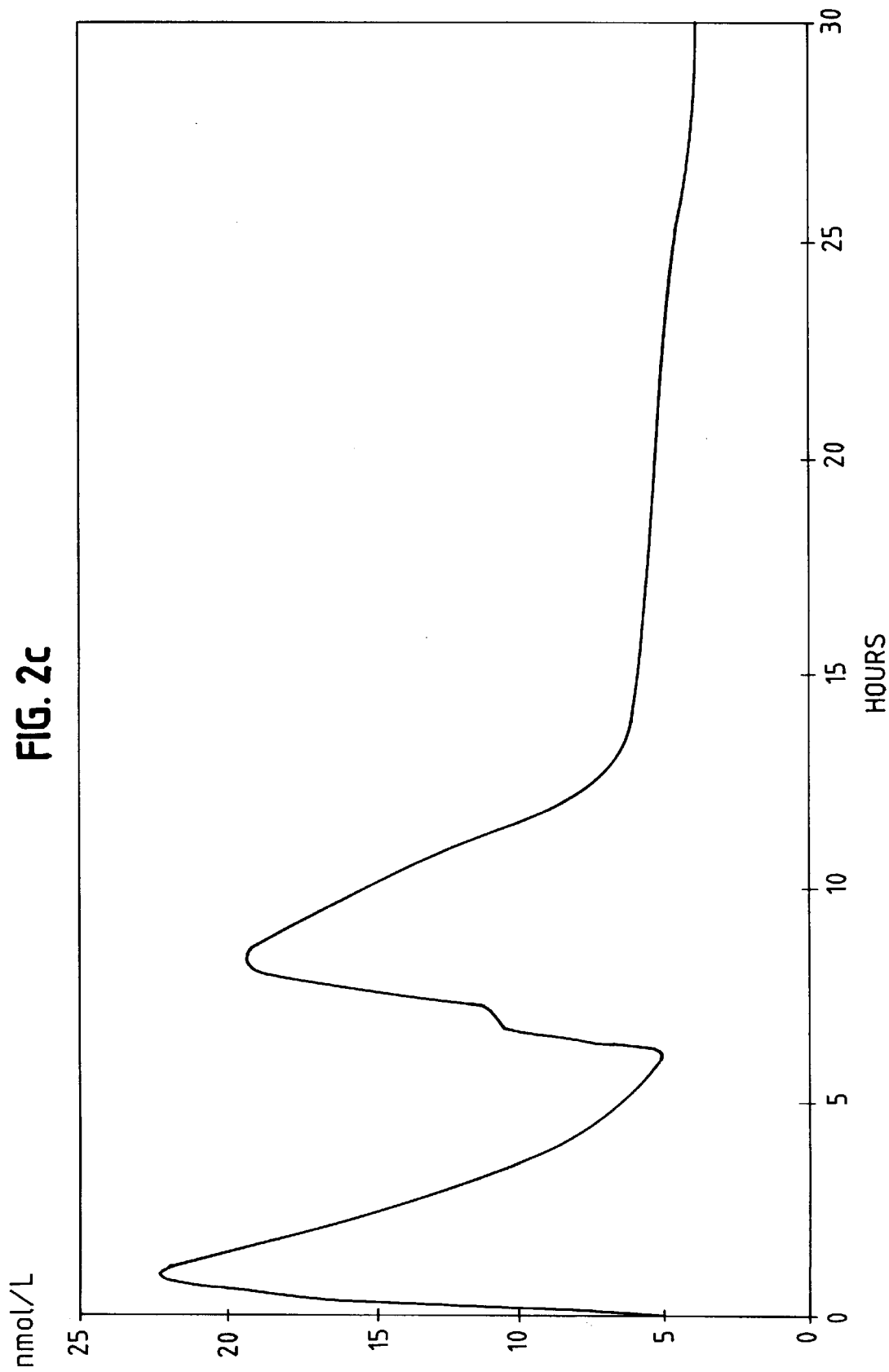
Figure 2D:
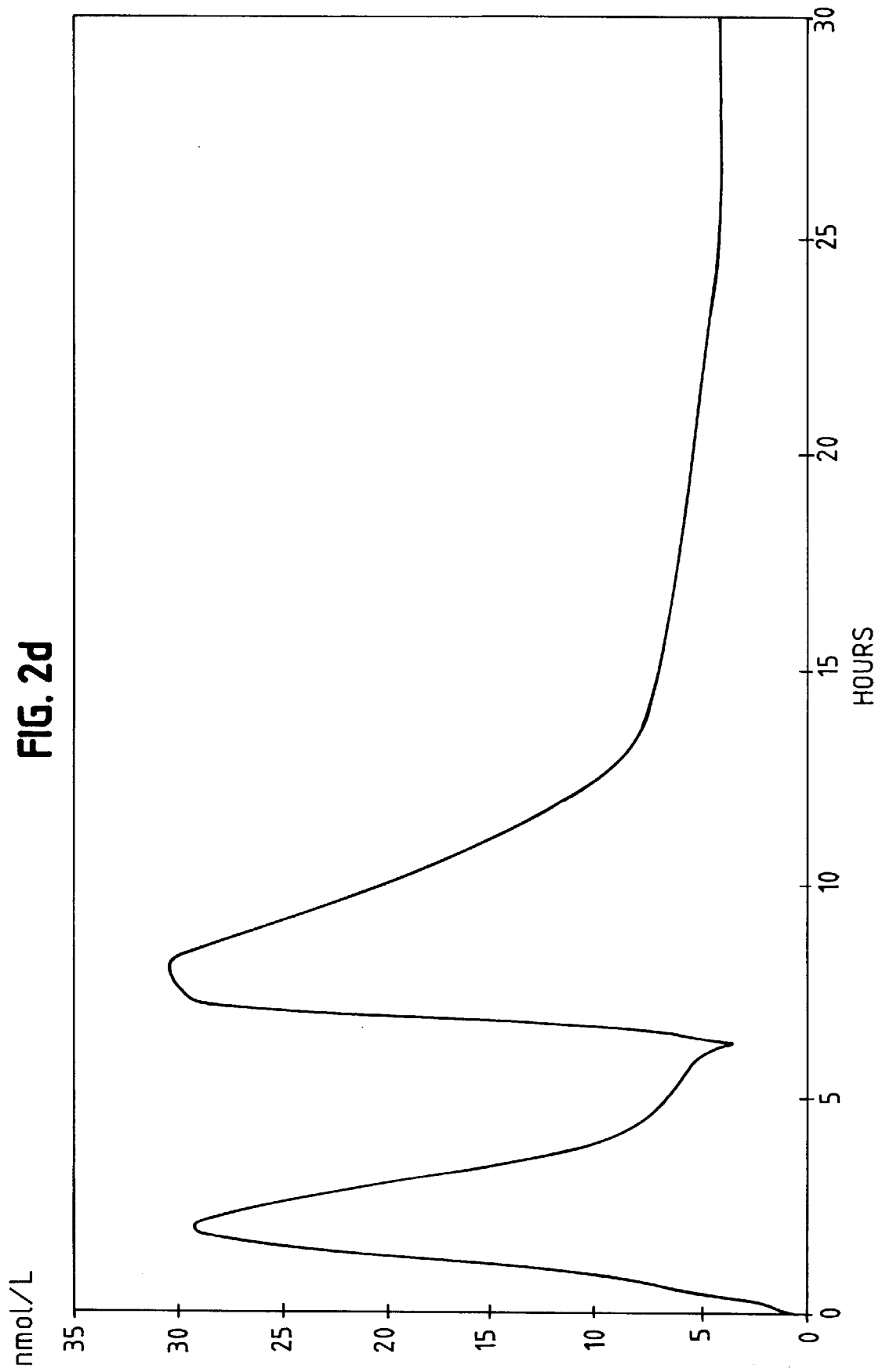

A preferred embodiment is shown in FIG. 1. The equipment is composed of three separate parts: A) a motility-driven head part 1, with a bore 2 running through it, used for pulling the tube 3 through the GI-tract, B) a flexible tube 3, fastened to said head part 1 in fluid connection with said bore 2, used for transport of liquid and/or gas, C) external interface 4, such as Luer Lok®, used for connection of the tube to a pumping or sucking device 5, in the simplest form an injection syringe.

A) The head part 1 is made of a relatively stiff plastics material and/or metal. The material in the head part should preferably be opaque to X-rays, at least to some extent, by which means its journey through and its present location in the GI-tract, at will, can be documented. The head part can have the shape of a typical oblong pharmaceutical gelatine capsule. Its length should be 1–4 cm and breadth 1–2 cm. Practical experiments have shown that a head part with a length of 2–3 cm and a diameter around 1 cm, corresponding to a volume around 2 mL, is a size suitable for swallowing and sufficiently large to enable the intestine to get a strong grip.

The tube 3 is connected, e.g. by means of a suitable glue, to the head part 1. An alternative manufacturing method is to cast plastics directly around the tube, using a mould of suitable dimensions.

B) The tube 3 must be sufficiently thin, flexible and smooth to be swallowed without causing nausea or throat irritation. Its flexibility enables the head part to pull it all along the GI-tract. A polymer, such as polyethene, is a suitable material. Especially the loops formed by the intestines can otherwise cause a very strong resistance and render transport of the tube all along the GI-tract impossible.

The length of the tube can vary dependent on the field of application. If the head part shall pass through the whole GI-tract, tube lengths of 5–6 m will be needed. The tube should not exceed 1 mm in diameter and for usefulness not have a smaller diameter than 0.4 mm. The inner diameter should be at least 0.2 mm, otherwise the resistance to flow will be too high. To resist pressure, the wall thickness should be at least 0.1 mm. A well proven tube is a polyethene tube with an outer diameter of 0.61 mm and an inner diameter of 0.28 mm (PORTEX Ltd, Hythe, England, ref. code 800/110/100). This tube fulfills the demand of being flexible, simultaneously admitting throughflow of liquid and/or gas when positioned in the GI-tract. This kind of tube might require special pretreatment of its surface to give a good adhesive capacity for the glue. The outer surface of the tube can be supplied with scale marks, e.g. for every 10 cm, to show the length of the tube that has been swallowed by the subject. By administering a fluid contrast medium, such as Omnipak® 300, through the tube it can be seen at fluoroscopy, and if enough contrast is given also the surrounding part of the gut can be seen.

In use the head part 1 is swallowed together with a length of the tube 3 which allows the head part to reach the stomach. If the experiment is planned to continue over a longer time period, the tube is first introduced through the nose into the mouth cavity, whereafter the head part is mounted and swallowed. After a certain time, the head part passes out through the pylorus due to the peristaltic movements of the stomach and reaches the duodenum. If the passage through pylorus is delayed (>1 hour), a motility-promoting drug, such as metoclopramide, may be injected. The normal peristaltic movements of the intestine then moves the head part along the intestinal tract together with the tube. The tube outside the body is kept in a small reel placed, for instance, in the breastpocket of a shirt or jacket. When the desired position has been reached, the tube is fastened for instance in one of the subject's teeth or in a piece of clothing; by doing so the head part is anchored in said position. If the requirements on exact positioning in the GI-tract are not very great, the position of the head part can be estimated by means of the length of the tube that the subject has swallowed. If higher precision is required, fluoroscopy can be used for exact localisation of the head part in the GI-tract. Then, if desired, a contrast medium can be injected through the tube to make the tube and, if more is injected, the surrounding gut visible to X-ray.

Once the exact length of tube required to reach the selected position in the GI-tract has been determined, on a later occasion another tube can be swallowed without the need for fluoroscopy which minimizes the X-ray dose to the subjects and makes possible self administration.

With this equipment administration can go on as long as desired, because the head part in principle can remain in the chosen position for an arbitrary length of time. The amount of substance given per time unit can be varied within wide limits. If a drug substance would be given for treatment of a local disease, the dose can be kept low because of localized administration. Very exact doses can be given, because the dead volume of the tube and head part is small and can also be rinsed after administration. Also the volumes of aspirated liquid are well defined because of the small dead volume. Normal food intake can occur and subjects can perform their normal activities.

When the head part has been kept in the selected position for the desired time, the tube is cut which causes the head part to be transported through the rest of the GI-tract and out of the body through the anus together with connected tube. Our experience has shown that it is possible to allow the head part and tube to stay in the gut for a long time (>24 hours); we have even reached as deep as into the colon sigmoideum without cutting the tube. When the head part is to enter the colon, it appears favourable to use a "light" head part, i.e. one that floats in water.

C) To the external interface 4 of the tube, in the simplest case, a common injection syringe 5 can be connected by means of which liquid and/or gas can be pressed through or liquid from the gut sucked. For a more advanced use of the system, for instance at use of various sensors or for automated control, the connected apparatus can of course be controlled using various soft-ware algorithms.

FIGS. 2a–2d show an experiment where drug substance has been supplied by means of the described equipment in an aqueous solution to four subjects on two levels in the gut: first in the upper part of the small intestine, then in the ileocaecal region:

a) In subject WM after administration of 3 mg at level 125 cm and 12 mg at level 234 cm.

b) In subject NBG after administration of 3 mg at 172 cm and 12 mg at 283 cm c) In subject JRO after administration of 3 mg at 114 cm and 12 mg at 223 cm d) In subject GAT after administration of 3 mg at 108 cm and 12 mg at 210 cm FIGS. 2a–2d illustrate the usefulness of the equipment to deliver drug substance to different levels of the gut.

MODIFICATIONS OF THE INVENTION

The invention can be modified in many ways within the framework of the enclosed claims. The normal use of the equipment implies that with the head part 1 in selected position within the GI-tract one can give a chosen fluid during arbitrary time or suck liquid from the gut. It is also possible to mix these functions through time multiplex. When doing so, it is essential to rinse the tube 3 with suitable rinsing solution at the change between aspiration and infusion, alternatively between infusion of different substances (e.g., for studies of interaction between substances).

By measurement of concentrations in body fluids after administration of substance(s), the equipment gives possibilities for measurements of uptake rate and absorption capability of various substances on different levels in the gut.

Thus, one can create individual "gut profiles" for various drugs which can be used, e.g. for a later development of pharmaceutical formulations. It is also possible to record such profiles upon addition of various potentially interacting substances. Deviating gut profiles, when diagnostic substances are added, can be used e.g. for diagnosis of inflammatory bowel disease or other disturbances in the normal function of the gut. Similarly, aspirates can be analysed for their contents of various compounds. If aspirates are taken on different levels, "profiles" for components in intestinal juice can be constructed.

The head part 1 can be constructed with space for a cargo in the form of sensors, chemical substance(s) and/or drugs. The available space is more than sufficient to contain sensors, e.g. for measurement of simple physical parameters, such as temperature and pressure, but also for measurements of pH, salts, enzyme activities, hemoglobin, blood corpuscles, bacteria, virus, cancer markers etc. Such head parts with sensors can of course also be used for measuring quite new physico-chemical "gut profiles" independent of administration but also for automatic sensor controlled delivery by letting the outsignal control the release of substance from the head part.

The signal from the sensors of the head part can be transmitted to the external world before, during, or after administration by means of a built-in wireless transmitter or by using electrical or optical conductors that have been added to the tube. The conductors can be placed in the actual tube lumen or in an extra conductor lumen within the tube (a thin tube with integrated electrical or optical conductors is commercially available).

Figure 4:
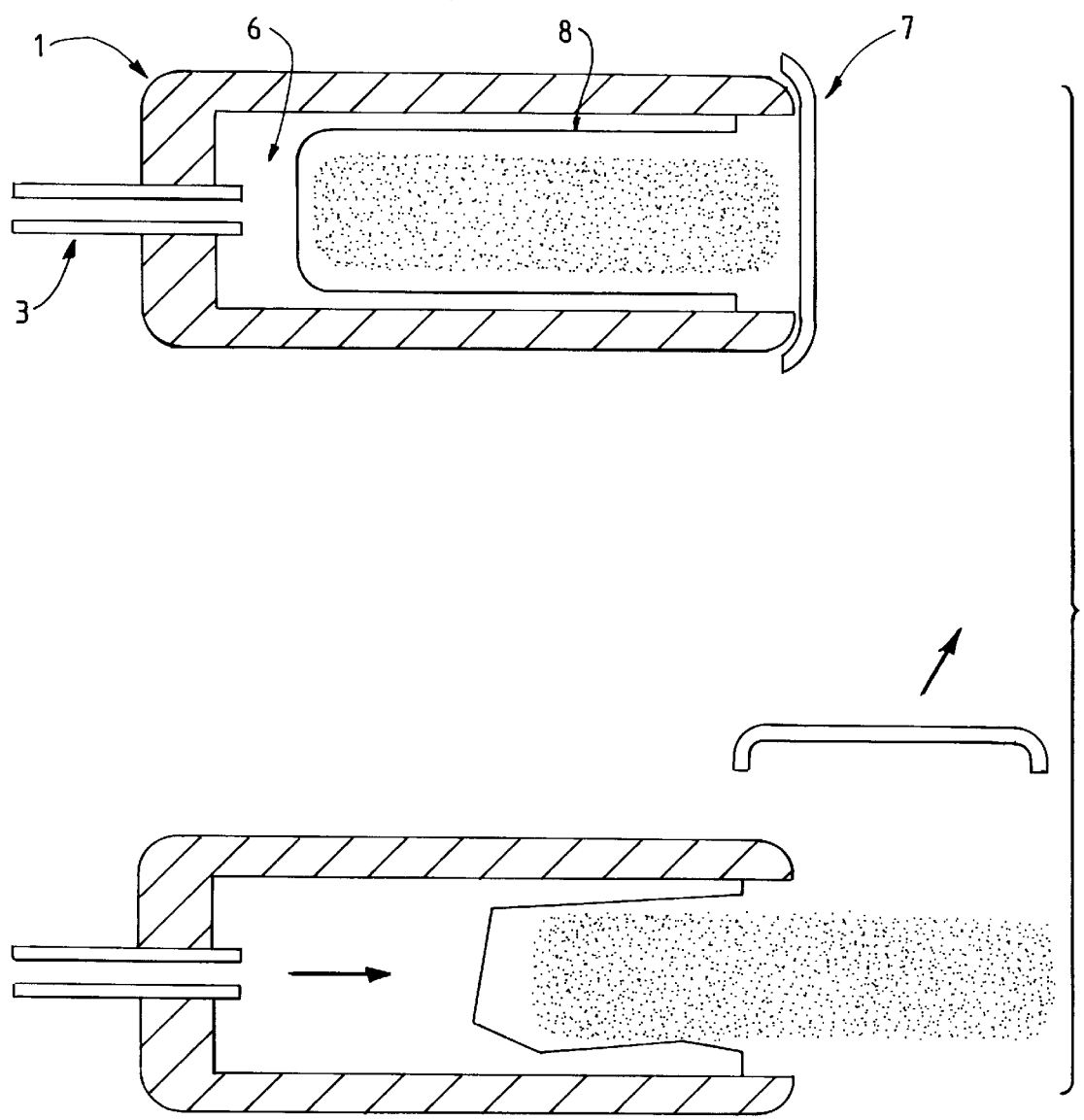
FIG. 4 shows a longitudinal section of another head part used for administration of substance powder.

By constructing the head part 1 somewhat different, also substances in powder form can be administered to a selected position in the gut. Such a head part can be constructed in two different ways:

a) FIG. 3: the head part 1 is made hollow and the tube ends in the cavity 6. Then the head part is filled with substance and is covered by a closing membrane 7. When the head part has reached the selected position in the gut, the pressure in the tube 3 is increased by introducing liquid or gas, for instance by means of a syringe in the external end of the tube, implying that the increased pressure in the head part 1 presses the membrane 7 away and the substance is released into the gut. Then the equipment can be used as usual, this means for instance for continuous infusion of substance solution.

b) FIG. 4: the head part 1 is made hollow and the tube 3 ends in the cavity 6. The inside of the head part is covered by a protective membrane 8 which is fastened at the frontal opening of the head part. Substance is filled into the pocket formed by the protective membrane and the head part is closed by a closing membrane 7. If the pressure is increased sufficiently in the tube 3 by injecting liquid or gas, the closing membrane 7 is removed and the head part opens. On further increase of the pressure, the membrane pocket inverts and the substance is emptied into the gut. The advantage with this method is that a complete rapid emptying of all powdered substance out of the head part is guaranteed; the drawback is that this kind of head part cannot be used for a following continuous infusion.

The control of the flow of liquid or gas in the tube 3 can of course be controlled by a computer which is programmed for a desired time sequence. The computer control can be made regarding performed measurements of gut profiles or reaction to signals from sensors in the head part.

At some inflammatory bowel diseases stenoses in the gut occur, which bears a risk that the head part can got stuck and not at all or only with difficulty can be transported through the GI-tract and out through the anus. By using a head part with hollow walls, externally flexible, for these cases, it can after the administration or aspiration procedures be pierced and then retracted out of the GI-tract through the mouth.

REFERENCES

In the order of appearance in the text:

B Hugemann. German patent DE 29 28 477 B2

R A Casper et al. U.S. Pat. No. 5,170,801

Kambara et al. U.S. Pat. No. 4,507,115

A Hemmati. Verh Dtsch Ges Inn Med 1969; 75:672–675

New York State University: Note in "Illustrerad Vetenskap" ("Illustrated Science"), No. 6, 1992, p. 65

H S Wolff and R F Russ. Paper in "Proceedings 3rd Int Conference on Medical Electronics" (1960)

A M Connell and E N Rowlands. Gut 1960; 1:266–272
F Bárány and B Jacobson. Gut 1964; 5:90–95
J T Farrar and J S Bernstein. Gastroenterology 1968; 54:770–771
A Uchiyama et al. Biotelemetry 1980; 5:47–49
A Lambert et al. Med Biol Eng Comput 1991; 29:191–196
E L Millard. U.S. Pat. No. 2,438,098
A L Kaslow and J J Saputo. U.S. Pat. No. 2,773,502
C Browning et al. Lancet 1981; ii:504–505
K Lindström et al. Patent application No. WO 92/057 59 A1
H Lennernäs et al. Pharm Res 1992; 9:1243–1250
S Bengmark et al. "Läkartidningen" (Physicians' Journal) 1989; 86:2204
F Lauterjung. Patent specification SE 448 671 B
P Deyhle et al. Endoscopy 1972; 4:155–157
R Seensalu. "Läkartidningen" (Physicians' Journal) 1993; 90:2449–2451

It is claimed:

1. A method for introducing a tube in order to deliver or remove one or more substances at positions in the gastrointestinal tract by letting a human subject or an animal swallow a firm body, hereafter called a head part, to which said tube is fastened and letting said head part be moved by peristalsis to desired positions, wherein:

said head part, which is provided with a bore or cavity running through it and being in fluid connection with said tube, stops at one or more selected positions in any part of the gastrointestinal tract by fixing said tube at the entrance into the body or outside the body;

said tube is marked to indicate length of the swallowed part of said tube in order to guide the finding of said selected position;

liquid or gas is delivered or aspirated through said tube and said bore or cavity running through said head part;

said head part and said tube leave the gut via the anus.

2. Method according to claim 1, wherein said tube is first entered into the mouth via the nose whereafter said head part is mounted and then swallowed.

3. Method according to claim 1 wherein exactly known volumes of liquid or gas are delivered or aspirated intermittently or continuously.

4. Method according to claim 1 wherein an exact amount of powdered substance, contained in said head part, is administered by means of liquid or gas pressed through said tube and said head part.

5. Method according claim 1 wherein signals are transmitted via said tube or via wireless signaling from the gut for measurement of physico-chemical parameters before, during or after administration or aspiration of liquid, gas, or powder, allowing construction of profiles for the measured parameters along the gut or for starting or stopping delivery of liquid, gas, or powder.

6. Method according to claim 5 wherein said signaling and construction of profiles are carried out without administration or aspiration.

7. Method according to claim 1 wherein absorption profiles along the gut are constructed by measurement of concentrations in body fluids after repeated administration of substances in dissolved or powder form.

8. Method according to claim 1 wherein said head part and tube are allowed to stay in the gut for longer than 24 hours.

9. The method according to claim 1, wherein said tube and the surrounding gut are made visible by X-ray or other radiation by injecting a contrast or radiation emitting medium through said tube and said head part.

10. The method according to claim 1, wherein said head part moves on to new selected positions and the described events are repeated.

11. Device for performance of the method described in claim 1 wherein said device comprises a firm head part through which runs a bore or cavity and to which a tube is fastened which is in fluid connection with the bore or cavity, the diameter of said head part being larger than that of said tube.

12. Device according to claim 11 wherein said head part is X-ray opaque.

13. Device according to claim 11 wherein said head part is floating in water.

14. Device according to claim 11 wherein said tube is made of a flexible polymer, such as polyethylene.

15. Device according to claim 11 wherein said tube has scale marks indicating the distance from lips or nostrils of said human subject or animal down to the position of said head part.

16. Device according to claim 11 wherein said head part has a length of 1–4 cm and a breadth of 1–2 cm.

17. Device according to claim 16, wherein said head part has a length of 2–3 cm and a breadth of about 1 cm.

18. Device according to claim 11 wherein said tube has an outer diameter of 0.4–1 mm, an inner diameter of at least 0.2 mm, and a wall thickness of at least 0.1 mm.

19. Device according to claim 16, wherein said tube has an outer diameter of 0.5–0.7 mm, an inner diameter of 0.25–0.35 mm and a wall thickness of about 0.15 mm.

20. Device according to claim 11 wherein said tube in its external end is designed to be tightly connected by an interface to an apparatus for propelling or sucking liquid or gas.

21. Device according to claim 20, wherein said tube in its external end has an interface which is a Luer-Lok® connection.

22. Device according to claim 11 wherein said tube in its other end has an arrangement for mooring said head part in a desired position by fixing said tube at the entrance into the body or outside the body.

23. Device according to claim 11 wherein said head part is externally delimited by flexible walls which can be pierced leading to collapse of the head part.

24. Device according to claim 11 wherein said head part in a cavity contains powdered substance protected from the environment by a membrane which can be removed by the pressure from liquid or gas supplied through said tube, thereby also releasing the powder into the gastrointestinal tract.

25. Device according to claim 11 wherein said head part carries one or more sensors for registration of physico-chemical parameters.

26. Device according to claim 25, wherein said tube contains one or more conductors making feasible electrical or optical signal transmittance.

27. Device according to claim 25, wherein said head part carries one or more transmitters for telemetric transmission to a receiver outside the body.

* * * * *